US012758389B2

(12) United States Patent
Jensen et al.

(10) Patent No.: US 12,758,389 B2
(45) Date of Patent: Oct. 13, 2026

(54) KNEE JOINT ENDOPROSTHESIS SET AND INSTRUMENTS

(71) Applicant: WALDEMAR LINK GmbH & Co. KG, Hamburg (DE)

(72) Inventors: Harm-Iven Jensen, Noer (DE); Helmut D. Link, Hamburg (DE)

(73) Assignee: WALDEMAR LINK GmbH & Co. KG, Hamburg (DE)

( * ) Notice: Subject to any disclaimer, the term of this patent is extended or adjusted under 35 U.S.C. 154(b) by 0 days.

(21) Appl. No.: 17/312,378

(22) PCT Filed: Dec. 10, 2019

(86) PCT No.: PCT/EP2019/084424
§ 371 (c)(1),
(2) Date: Jun. 9, 2021

(87) PCT Pub. No.: WO2020/120475
PCT Pub. Date: Jun. 18, 2020

(65) Prior Publication Data

US 2022/0015914 A1 Jan. 20, 2022

(30) Foreign Application Priority Data

Dec. 10, 2018 (EP) .................................... 18211379

(51) Int. Cl.
*A61F 2/38* (2006.01)
*A61F 2/30* (2006.01)
*A61F 2/46* (2006.01)

(52) U.S. Cl.
CPC ............ *A61F 2/3859* (2013.01); *A61F 2/389* (2013.01); *A61F 2/461* (2013.01); *A61F 2/4657* (2013.01);
(Continued)

(58) Field of Classification Search
CPC ........ A61F 2/3859; A61F 2/389; A61F 2/461; A61F 2/4657; A61F 2002/30125;
(Continued)

(56) References Cited

U.S. PATENT DOCUMENTS 4,167,047 A * 9/1979 Grundei .................... A61F 2/38 623/20.34
4,404,691 A * 9/1983 Buning ................. A61F 2/3607 623/20.15
(Continued)

FOREIGN PATENT DOCUMENTS

DE 3336005 C2 * 9/1993 ............... A61F 2/28
DE 10036636 A1 3/2001
(Continued)

OTHER PUBLICATIONS

Translation of Klaus-Dieter (EP0410237) (Year: 1991).*
(Continued)

*Primary Examiner* — Christopher D. Prone
(74) *Attorney, Agent, or Firm* — Chiesa Shahinian & Giantomasi PC

(57) ABSTRACT

A knee joint endoprosthesis set including modular knee joint endoprostheses in different sizes. Each knee joint endoprosthesis includes a tibial component. The femoral component includes a joint element for articulated cooperation with the tibial component and comprises a shaft for anchoring in the femur. The set includes shafts in different sizes. In the femoral component, the shape of the shafts tapers from a distal end, facing toward the joint element, to a proximal free end of the shaft. An oval cross-section is provided at the distal end, and a round cross-section is provided at the proximal free end of the shaft.

21 Claims, 7 Drawing Sheets a) b)

(52) U.S. Cl.
CPC ............... *A61F 2002/30125* (2013.01); *A61F 2002/30327* (2013.01); *A61F 2002/30538* (2013.01); *A61F 2002/30616* (2013.01); *A61F 2002/3863* (2013.01); *A61F 2002/4662* (2013.01); *A61F 2002/4668* (2013.01)

(58) Field of Classification Search
CPC .. A61F 2002/30327; A61F 2002/30538; A61F 2002/30616; A61F 2002/3863; A61F 2002/4662; A61F 2002/4668; A61F 2002/30827; A61F 2002/30836; A61F 2002/30879; A61F 2/38; A61B 2090/062
See application file for complete search history.

(56) References Cited

U.S. PATENT DOCUMENTS

| | | | | |
|---|---|---|---|---|
| 4,834,758 A * | 5/1989 | Lane | A61F 2/3607 | 623/20.24 |
| 4,846,839 A | 7/1989 | Noiles | | |
| 5,342,366 A | 8/1994 | Whiteside et al. | | |
| 5,464,406 A | 11/1995 | Ritter et al. | | |
| 6,071,311 A * | 6/2000 | O'Neil | A61F 2/30734 | 623/20.15 |
| 6,254,640 B1 | 7/2001 | De Cesaris et al. | | |
| 6,673,077 B1 | 1/2004 | Katz | | |
| 9,918,842 B1 * | 3/2018 | Whiteside | A61F 2/38 | |
| 10,716,686 B2 * | 7/2020 | Schrader | A61F 2/3859 | |
| 2005/0107883 A1 * | 5/2005 | Goodfried | A61F 2/3859 | 623/20.15 |
| 2006/0142778 A1 | 6/2006 | Dees | | |
| 2007/0112433 A1 * | 5/2007 | Frederick | A61F 2/30942 | 623/908 |
| 2008/0140214 A1 * | 6/2008 | Hedley | A61F 2/4684 | 623/20.35 |
| 2009/0005875 A1 * | 1/2009 | Koenemann | A61F 2/3859 | 623/20.35 |
| 2013/0211531 A1 * | 8/2013 | Steines | A61F 2/3859 | 623/20.14 |
| 2014/0142714 A1 * | 5/2014 | Wright | A61F 2/3859 | 623/20.31 |
| 2020/0397587 A1 * | 12/2020 | Magagnoli | A61F 2/30724 | |
| 2021/0282933 A1 * | 9/2021 | Sutherland | A61K 31/165 | |

FOREIGN PATENT DOCUMENTS

| | | | | |
|---|---|---|---|---|
| EP | 0410237 A1 | 1/1991 | | |
| FR | 0201407 A1 * | 11/1986 | A61F 2/36 | |
| FR | 0865777 A1 * | 9/1998 | A61F 2/3609 | |
| FR | 2889444 A1 * | 2/2007 | A61F 2/36 | |
| FR | 2976176 A1 * | 12/2012 | A61F 2/3886 | |
| WO | WO 83/02555 A1 | 8/1983 | | |
| WO | WO 98/42279 A1 | 10/1998 | | |
| WO | WO-2018200127 A1 * | 11/2018 | A61F 2/30771 | |

OTHER PUBLICATIONS

Translation of Montagne (EP0201407A1) (Year: 1986).*

Definition of "round" retrieved from Oxford Languages (Year: 2024).*

International Search Report and Written Opinion mailed Apr. 17, 2020 in corresponding International Application No. PCT/EP2019/084424 and the English Translation of the International Search Report ..

Search Report and Written Opinion issued in corresponding European Application No. 18211379.5 dated Aug. 13, 2019.

* cited by examiner a) b)

a) b)

KNEE JOINT ENDOPROSTHESIS SET AND INSTRUMENTS

CROSS-REFERENCE TO RELATED APPLICATIONS

This application is the National Stage entry under 35 U.S.C. § 371 of International Application No. PCT/EP2019/084424 filed on Dec. 10, 2019, published on Jun. 18, 2020 under Publication Number WO 2020/120475 A1, which claims the benefit of priority under 35 U.S.C. § 119 of European Patent Application Number 18211379.5 filed Dec. 10, 2018, the entireties of which are herein incorporated by reference.

The invention relates to a set of knee joint endoprostheses, specifically the femoral components of the knee joint endoprostheses, and an insertion tool for implanting the femoral components at the distal end of a femur. The femoral component of a knee joint endoprosthesis cooperates with a tibial component; these two components basically form the knee joint endoprosthesis. The set comprises knee joint endoprostheses in different sizes.

Knee joint endoprostheses for total replacement of a natural knee joint have already been known for a long time. Typically, a knee joint endoprosthesis has a femoral component and a tibial component which, during implantation by the surgeon, are inserted at the distal end of a femur and correspondingly at the proximal end of the tibia. The femoral component cooperates with the tibial component in such a way that it simulates the hinge function of the natural knee joint. For this purpose, the two components generally each have a joint piece and a shaft for anchoring. Such knee prostheses are also referred to as total knee prostheses.

To adapt to different anatomical conditions in patients, knee joint endoprostheses are available in several sizes. In the case of modular knee joint endoprostheses that are manufactured in series, the components can be obtained comparatively inexpensively in different sizes, but the adaptation to the respective anatomical conditions is often unsatisfactory. It may therefore be necessary to embed and fix the prosthesis with cement in the medullary canal of the femur. However, this often has the disadvantage of inadequate long-term stability. Loosening in the cement can occur, as a result of which the shaft of the femoral component is no longer securely anchored in the femur. In many cases, particularly with loss of condylar bone, the shaft is generally crucial for load transmission and essential for guiding the prosthesis. In the event of loosening, it can no longer satisfy any of these functions, with the result that the prosthesis fails. A follow-up operation is then required. This problem can be countered by producing the shaft individually to adapt to the respective anatomical conditions. This can be done after a CT scan of the femur, in order thereby to determine the individual shape of the medullary canal and then to shape the shaft. However, this then entails a custom-made model. Although this has the advantage of a good fit and therefore of good long-term stability, it is very expensive.

The object of the invention is to combine the advantages of the two different approaches with each other.

The solution, according to the invention, lies in the features of the independent claims. Advantageous developments are the subject matter of the dependent claims.

In a knee joint endoprosthesis set comprising modular knee joint endoprostheses in different sizes, each knee joint endoprosthesis comprising a tibial component for anchoring at a proximal end of the tibia, a femoral component for anchoring at a distal end of the femur, the femoral component comprising a joint element for articulated cooperation with the tibial component and comprising a shaft for anchoring in a medullary canal of the femur, the set comprising shafts in different sizes, provision is made according to the invention that, in the femoral component, a shape of the shafts is chosen such that it tapers from a distal end, facing toward the joint element, to a proximal free end of the shaft, and is designed with an oval cross-section at the distal end and with a round cross-section at the proximal free end of the shaft, wherein an ovality defined by the oval cross-section increases as the size of the shafts increases. Here, the different sizes are preferably graded according to the ovality.

The invention has recognized that, by changing the cross-sectional design of the shaft in the claimed manner, it is possible to achieve a particularly good adaptation of the different sizes to the anatomical conditions of the femur and of its medullary canal. The oval shape at the distal end, in combination with the transition to a round configuration at the free end, results in a rotation-proof and firm fit of the femoral component in the bone. The shaft thus advantageously becomes a load-bearing shaft and does not simply take on a mere guiding function, as is predominantly the case in the prior art, but also ensures the retaining and fastening function. This advantage can be exploited to form a set, wherein shafts manufactured in series in a small number of predetermined sizes permit a secure anchoring comparable to that which has hitherto been the reserve mainly of custom-made shafts adapted to the particular anatomy of the patient. This results in much better compatibility and long-term stability of the prostheses. The risk of follow-up surgery, with its inherent complications, is reduced, particularly also for obese patients who, as experience shows, are particularly subject to the risk of loosening of an implant.

It is a merit of the invention to have recognized that it is the ovality that is decisive for the size gradation of the shafts. It thus departs from previous approaches, which typically considered the shaft length as a decisive parameter for the size. It is completely surprising that a particularly good fit can be achieved with a manageable number of sizes.

Some terms used are first of all explained below:

An ML direction is understood to mean a direction running from medial to lateral. It runs transversely with respect to the sagittal plane of a body and is thus a transverse direction. In anatomy, it is also referred to as the transverse axis and thus corresponds largely (although not necessarily exactly) to the axis for the flexion movement of the knee joint.

An ML dimension is understood to mean a dimension in the ML direction, for example an extent of the ovality in the ML direction.

An AP direction is understood to mean a direction running from anterior to posterior, that is to say from the front to the back of the body. This direction is transverse to the frontal plane of the body. In anatomy, it is also referred to as the sagittal axis and is perpendicular to the sagittal plane.

An AP dimension is understood to mean a dimension in the AP direction, for example an extent of the ovality in the AP direction. All of the aforementioned directions relate to the installed (implanted) state of the endoprosthesis.

An ovality is defined by its oval cross-section. A size of the ovality is dependent on the size of the cross-section. An ovality degree of an ovality is formed by a ratio of its longer axis to its shorter axis, for example, by the ratio between its ML dimension and its AP dimension. The greater this ratio, the greater the degree of ovality and the greater the deviation from the circular shape.

A round cross-section is understood to mean a substantially circular configuration.

An equivalent diameter is understood to mean the diameter in the case of a circular shape and to mean an average diameter in the case of a non-circular shape. A possible undersize, as can be present in the case of shafts designed for cemented implantation in comparison to shafts of the same size designed for cementless implantation, is not taken into consideration in the determination of the equivalent diameter.

The oval cross-section preferably has an ovality whose major axis lies in the ML direction and whose minor axis lies in the AP direction, wherein preferably a ratio of the long axis to the short axis lies in the range of between 1.1 and 1.4. With this special configuration of the ovality in the surprisingly narrow band of the axial relationship, it is possible, as the invention has recognized, to achieve an outstandingly good fit. This can be further enhanced by making the ovality elliptical.

According to a particularly preferred embodiment of the invention, a configuration of the ovality is provided in which a degree of ovality differs between the shafts of different sizes, specifically in such a way that the degree of ovality increases as the size of the shafts increases. Here, the surprising realization is exploited that it is advantageous to change the ovality in a defined manner across the different sizes. This is expediently done in such a way that the ovality between the different sizes is not the same in shape (and then only differs in terms of its size), but that the ovality should be systematically of variable shape. It is a merit of the invention to have recognized that it is in particular the degree of ovality that offers a quite excellent correlation to the different sizes of the shaft. With this configuration, the invention departs from the previous approaches, which predominantly considered the shaft length as the decisive parameter for the size. The pure thickness of the shaft is also not used as a decisive parameter for the size. The prior art contains no indication whatsoever of creating a set of shafts of different sizes for knee joint endoprostheses where each size has its own different degree of ovality. It is completely surprising that a particularly good fit can be obtained with a manageable number of sizes.

The knee joint endoprosthesis is modular, wherein shafts of different sizes are provided, which can be selectively connected to the joint component.

The shafts preferably each have a lateral surface which is designed to bear against an inner wall of the medullary canal. Additionally, or alternatively, the shafts can each have a lateral surface which corresponds to a conical transition body between an oval, in particular elliptical, cross-section at one end and a circular cross-section at the other end. This means that contact can be achieved across a large surface area, which leads to favorable introduction of loads into the bone and distribution of pressure on the bone. The load-bearing capacity and the long-term stability can thus be improved.

The shafts are designed such that they have a modulus of elasticity in the range of from 70 to 120 GPa, especially if they are made of titanium and cement-free. They are therefore within the physiologically favorable range and can on the one hand ensure good force transmission to the bone and on the other hand prevent bone degeneration, as could easily occur if the modulus of elasticity were otherwise unsuitable (Wolff's law of transformation).

Furthermore, the shafts can advantageously be curved, i.e. weakly curved with a curvature that has a radius of curvature of at least 1000 mm. With such a relatively weak curvature, a clear positioning of the shaft and thus of the knee joint endoprosthesis as a whole can be achieved in the bone. Here, the invention makes use of the fact that typically the medullary canal of the femur is not wholly straight but has a slight curvature. By virtue of the shaft likewise having a curvature, a preferred position is thus created. This not only ensures an improved contact and thus improved force transmission between shaft and bone, but also a positionally accurate implantation. Any curvatures are preferably designed such that they have different sizes in the AP direction and ML direction. It is particularly preferable if the shafts are more strongly curved in the AP direction. This can even go to the extent that the shafts have no curvature at all in the ML direction, i.e. are not curved. In particular, the shafts are preferably curved one-dimensionally; there is, therefore, only one plane of curvature. This results in a relatively simple basic shape that can be produced efficiently and yet permits good permanent fastening.

It is expedient to design the shafts as short shafts with a length of less than 7 times an equivalent diameter of the shaft at the distal end. A short shaft of this kind affords the advantage that on the one hand it has a relatively large cone angle and thus allows more universal adaptability; on the other hand, this affords the particularly valuable advantage, for successful implantation and for the health of the patient, that the short shaft penetrates less deeply into the bone, and thus the risk of bacteria or other germs penetrating deep into the bone is reduced. The short shafts are therefore expediently designed to be even shorter, preferably with a length that is less than five times, but more preferably more than twice, the equivalent diameter at the distal end of the shaft. The depth of penetration of the prosthesis is thus further reduced, the minimum length ensuring that there is still a sufficiently large surface area available for force transmission and that there is sufficient guidance.

The free end on the shaft expediently has a rounded dome shape. Such a shaft tip, resembling a semispherical shape for example, permits simpler introduction and insertion of the shaft into the medullary canal of the femur.

Furthermore, such a design is atraumatic and protects the sensitive interior of the bone. It is particularly useful if the free end is rounded all the way around.

According to a further particularly advantageous embodiment of the invention, adapters are provided which connect the joint element to one of the shafts, wherein adapters of different lengths are preferably provided. A design of the adapters as plug-in adapters is expedient. In this way, by choosing a suitable adapter, a change of length can be achieved without the need for another shaft. Thus, a more precise adaptation to the respective anatomical conditions of the patient can be achieved in a simple manner and without requiring additional sizes for the knee joint endoprosthesis set according to the invention. The adapters are advantageously designed to be adjustable in terms of their angle, specifically such that they can be locked in their angular position. A defined relative rotation between shaft and joint element can thus be set and secured. This likewise improves the adaptability of the knee joint endoprosthesis set according to the invention to the respective anatomical conditions of the patient, without additional shaft models being needed for the set. For this purpose, the adapter is expediently designed as a double cone or is provided with multiple teeth. The latter option affords the advantage of a form-fit angle adjustment, while the former affords the advantage of stepless adjustability of the angle.

The knee joint endoprosthesis set expediently comprises shafts for fastening by means of cement and also shafts for cementless fastening. It is thus possible to react flexibly to various requirements. Here, the shafts for fastening by means of cement preferably have a predefined undersize relative to the corresponding shafts for cementless fastening. This makes it possible for cementless shafts to be exchanged for shafts of more or less the same size that are to be cemented, if necessary even during surgery. The range of application of the knee joint endoprosthesis set according to the invention thus broadens considerably. Provision can be made here that the shafts for fastening by means of cement have a smooth lateral surface, which is optionally provided with a small number of furrows (maximum 5), whereas the shafts for cementless fastening preferably have a corrugated lateral surface. Typically, in the case of a corrugation of the lateral surface, at least 16, preferably at least 20, corrugation strips are arranged extending axially over the circumference of the shaft. The corrugation in particular increases the initial fastening safety in the case of cementless implantation, and the smooth design of the lateral surface or the small number of furrows can accordingly improve a cemented fastening.

In terms of size, the shafts are preferably graded according to the ML dimension, specifically in a regular manner. A gradation in regular steps has proven useful. The regularity can be provided, for example, by a progression, in particular a linear progression, a logarithmic progression or a geometric progression. Regular gradation on the basis of a module dimension is particularly preferred. The module dimension (a) corresponds to a size step between two directly successive sizes; the smallest and largest size of the set is also determined on the basis of the module dimension. This can be done, for example, in such a way that the smallest size corresponds to approximately 10 to 15 times the module dimension a (for example 13·a) and the largest size corresponds approximately 20 to 30 times the module dimension a (for example 23·a). By specifying just one dimension, namely the module dimension a, it is thus possible to achieve an appropriate gradation and thus selection of the sizes for the shafts of the set. It is particularly preferred if the shafts extend approximately in the size ratio in the range of 1:2, and the module dimension a is preferably chosen such that there are between 8 and 14, more preferably between 10 and 12, different sizes.

The invention moreover extends to an instrument kit for implanting a femoral component of a knee joint endoprosthesis from the knee joint endoprosthesis set. As has already been described above, the femoral component of the knee joint endoprosthesis has a shaft and a joint element. The instrument kit comprises a tool with which a cavity, dimensioned to receive the shaft, is formed at the distal end of the medullary canal of a femur, a gauge for producing a seat for the joint element at the distal end of the femur, a depth-measuring device for determining a positioning of the shaft in the cavity created to receive the shaft, and an insertion instrument for implanting the femoral component at the distal end of the femur, the depth-measuring device being designed to indicate a required length of the shaft and/or of an adapter for fastening the shaft to the joint element. With this instrument kit, the depth-measuring device can be used to precisely position the shaft in the bone. It will be understood that the depth-measuring device is matched to the different sizes of the set. The depth-measuring device thus allows the surgeon to precisely position the shaft in the cavity. This increases the fitting accuracy, and the risk of malfunction of the knee joint endoprosthesis is effectively counteracted.

In addition, an angle-measuring device can be provided. It is designed to determine an angle of rotation of the shaft within the medullary canal. Thus, particularly in the case of a curved shaft which, as described above, adopts a preferred position in the medullary canal, the angular position thereof can be detected and determined. This angle must also be set for the shaft of the knee joint endoprosthesis during implantation in order thereby to achieve an optimal fit. Since the preferred direction can be rotated both to the left and to the right, with left and right alternately standing for medial and lateral depending on the body side, a separate indicator is expediently provided for a rotation direction of the shaft within the medullary canal. With this indicator, the risk of confusion between left and right or between medial and lateral is greatly reduced, since only the indicator needs to be referred to and thus noted. The indicator can be designed, for example, as a punched marking or another structural element on the angle-measuring device. The depth-measuring device and the angle-measuring device are advantageously designed as a combined element. This reduces the number of parts and simplifies handling.

A separate alignment gauge can also be provided. It is expediently to be arranged at the transition between joint element and shaft, and it is designed to determine a relative rotation between shaft and joint element. Thus, the angle determined by the angle-measuring device for a rotation of the shaft in the medullary canal can be controlled as a relative rotation between shaft and joint element, preferably in such a way that a relative rotation is set by means of the adapter. In this way, the shaft is then precisely aligned such that the joint element is correctly oriented when the shaft has located itself in its preferred position. Fitting of the knee joint endoprosthesis at a precise angle is thus made considerably more reliable and easier.

The invention also relates to an individual knee joint endoprosthesis from the knee joint endoprosthesis set according to the invention.

The invention further extends to a corresponding method for implanting a femoral component of a knee joint endoprosthesis from the knee joint endoprosthesis set, wherein the femoral component has a shaft and a joint element, characterized by preparing a knee joint for the implantation of a knee joint endoprosthesis, excavating a cavity at the distal end of the femur for receiving the shaft, producing a seat for the joint element at the distal end of the femur by means of a gauge, determining a positioning of the shaft in the cavity, and inserting the femoral component with its shaft and the joint element, wherein a suitable size of the shaft is selected from the knee joint endoprosthesis set.

For a more detailed explanation of the method, reference is made to the above description.

The invention is described below by way of example with reference to advantageous embodiments of the invention and by reference to the drawing, in which:

FIG. 1 shows a perspective view of a knee joint endoprosthesis in the implanted state on the knee joint;

FIGS. 2*a, b* show schematic frontal and lateral views of the femoral component of a knee joint prosthesis according to an illustrative embodiment of the invention;

FIGS. 3*a, b* show a frontal and a lateral view of a shaft of the femoral component according to the illustrative embodiment of the invention;

Figure 6:
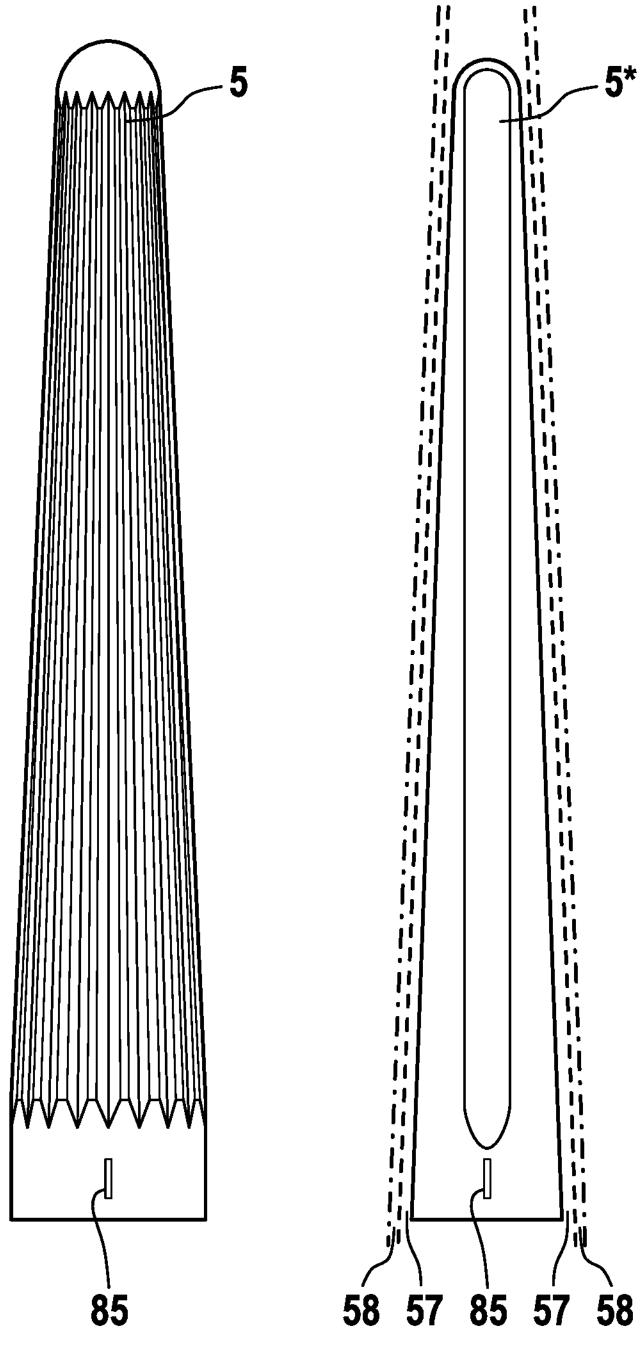
Figure 7:
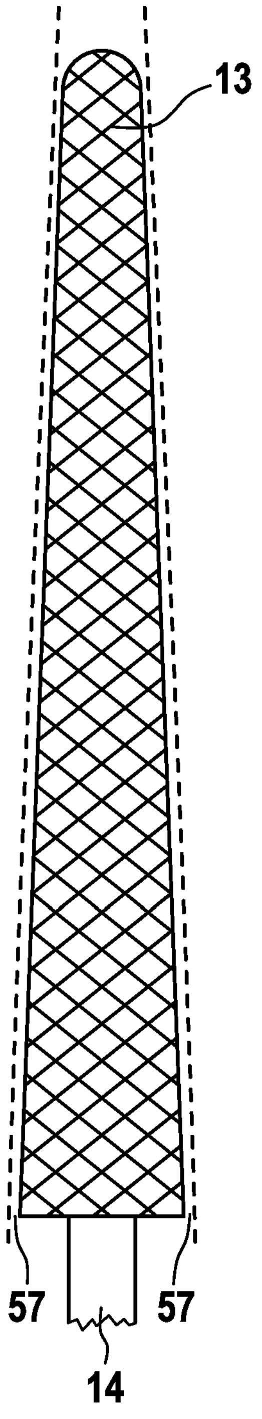
Figure 8:
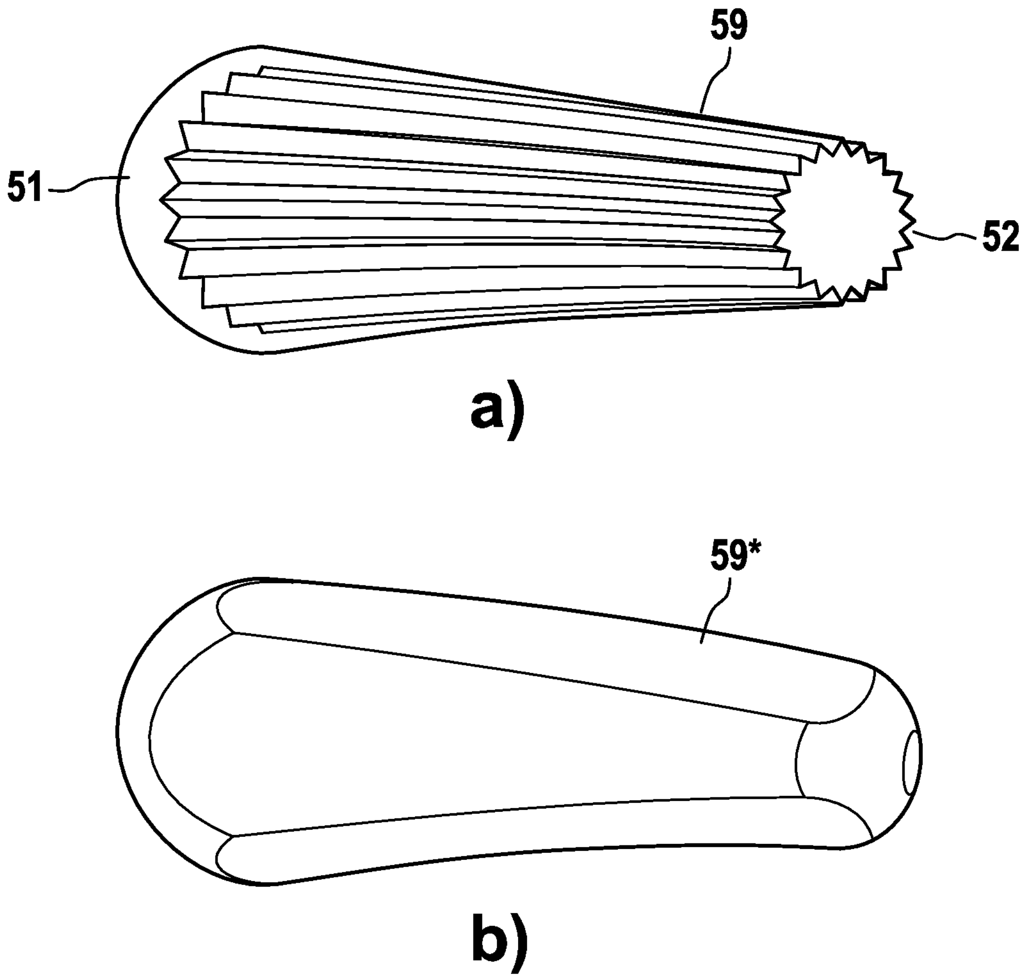

FIGS. 6*a, b* show a shaft of the same size for cementless and for cemented implantation, respectively;

FIG. 7 shows a rasp matching the shafts according to FIG. 6;

FIGS. 8*a, b* show perspective views of the shafts according to FIGS. 6*a, b;*

Figure 9:
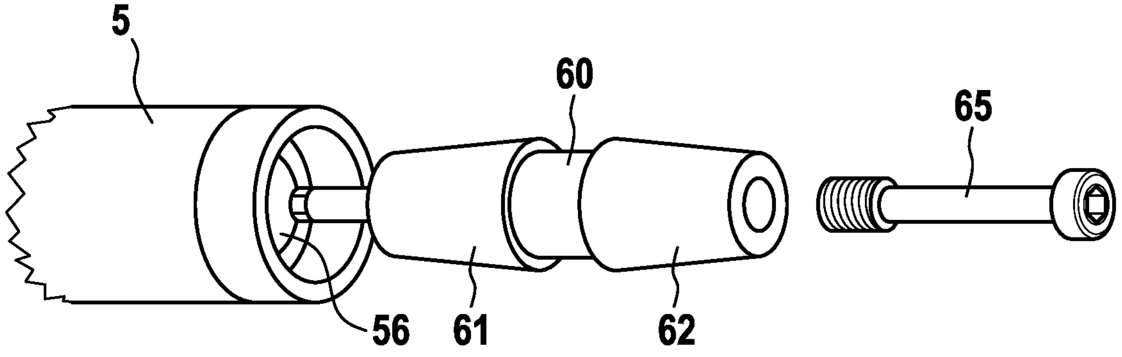
Figure 10:
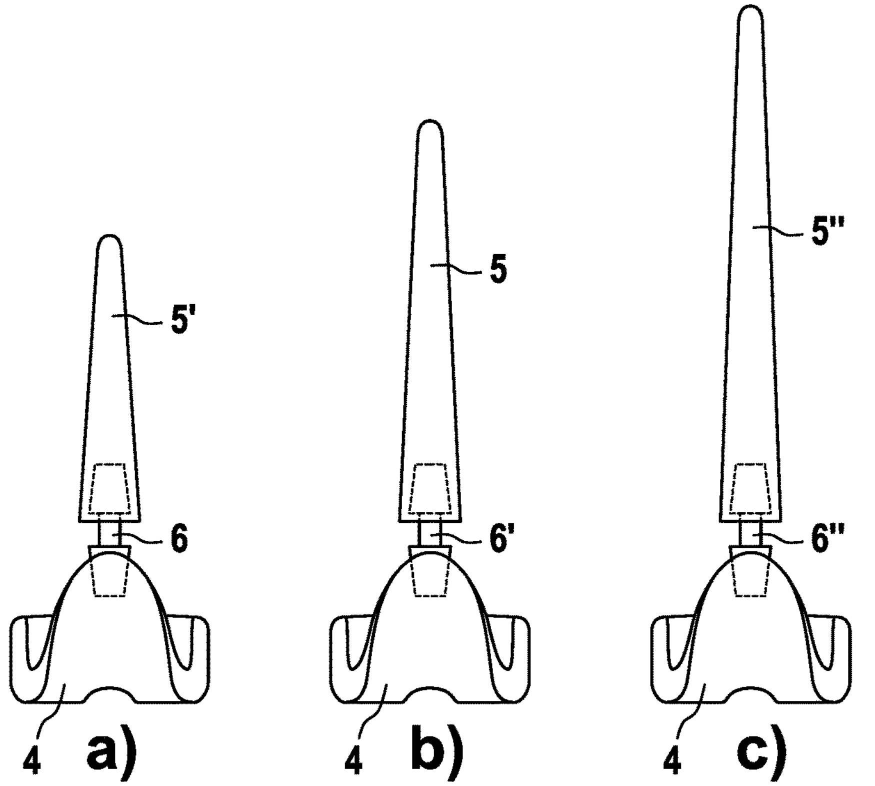
Figure 11:
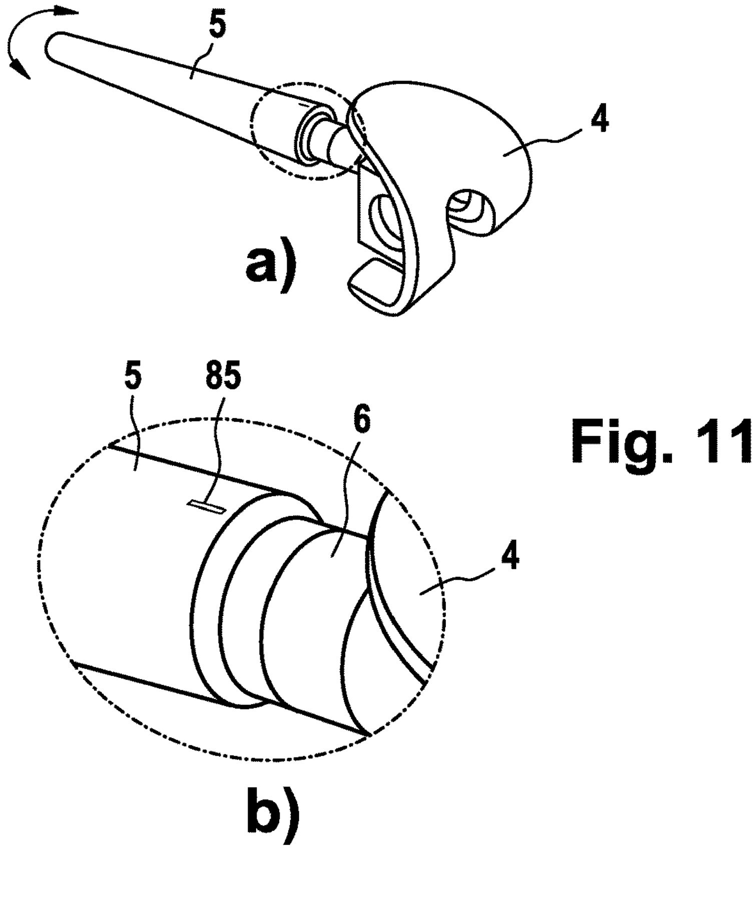
Figure 13:
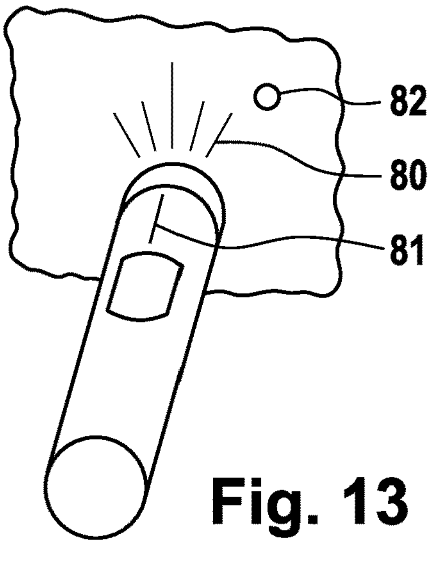

FIG. 9 shows an adapter for arrangement between the shaft and joint element of the femoral component;

FIGS. 10*a, b, c* show adapters of various lengths combined with shafts of different lengths;

FIGS. 11*a, b* show a perspective view of the adapter with a detailed representation;

FIGS. 12*a, b* show perspective views of a combined depth-measuring and angle-measuring device;

FIG. 13 shows a detailed representation of the depth-measuring and angle-measuring device; and FIGS. 14*a-f* show views of different steps for implantation of the knee joint endoprosthesis according to the illustrative embodiment.

Figure 1:
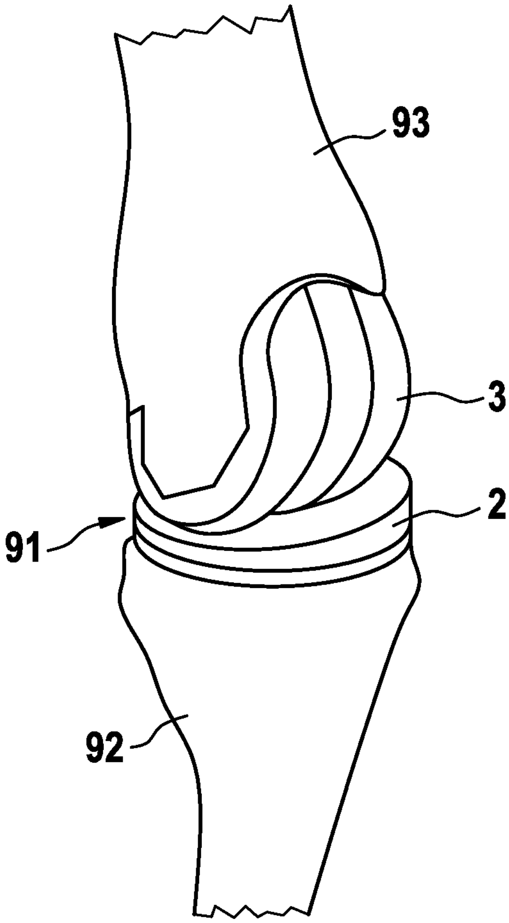

A knee joint endoprosthesis is shown in FIG. 1 in the implanted state on the knee. This is a cutout view and shows a region of the thigh around a knee joint 91. The (upper) proximal end of a tibia 92 and the (lower) distal end 93 of the femur can be seen. The natural knee joint is replaced by a knee joint endoprosthesis which comprises a tibial component 2 and a femoral component 3, which cooperates with the latter in an articulated manner.

Figure 2:
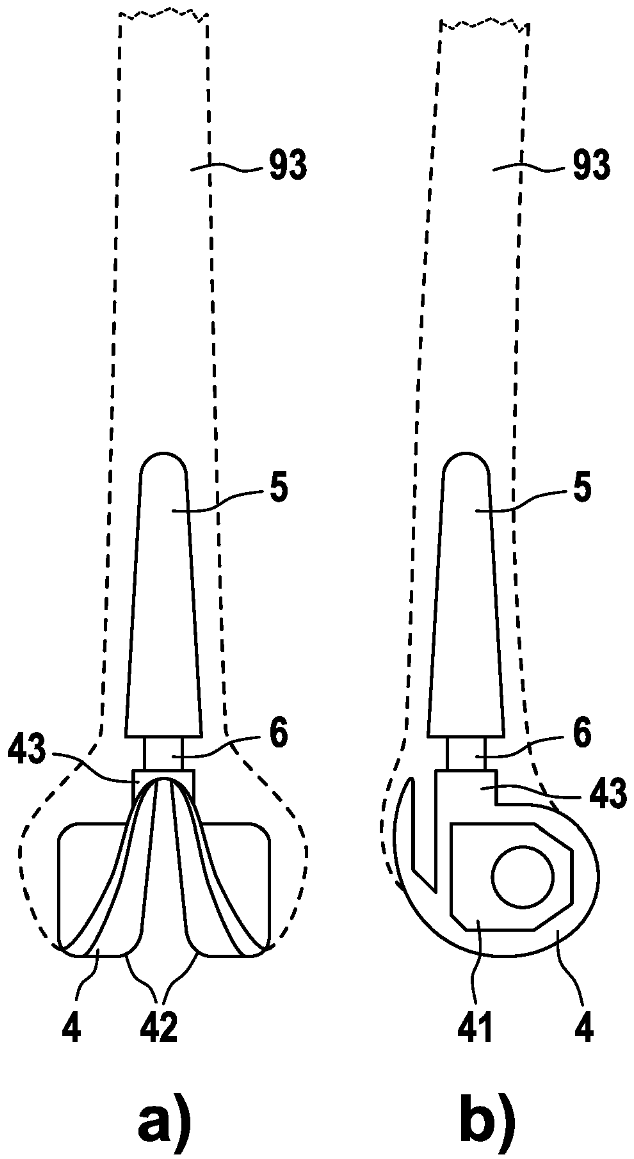

The knee joint endoprosthesis as a whole and its tibial and femoral components 2, 3 have a modular structure. The structure of the femoral component 3 is explained below. The main components of the femoral component 3 are shown in FIG. 2, which shows a frontal view in FIG. 2*a* and a lateral view in FIG. 2*b*. The femoral component 3 inserted at the distal end of the femur 93 comprises, as its main components, a joint element 4, a shaft 5 and an adapter 6. The joint element 4 has outwardly directed condyle elements 42 for the articulated interaction with the tibial component 2. The condyle elements 42 are arranged on a box-like main body 41 which, at its proximal end, comprises a coupling piece 43 for connection to the shaft 5.

The shaft 5 is connected to the joint element 4 via an adapter 6. In the illustrative embodiment shown, it is a pin-like adapter 6, which is provided with a double cone. It is inserted with its distal end into the coupling piece 43 and with its proximal end into a corresponding seat 56 (see FIG. 9) on the shaft 5. The generally cone-shaped shaft 5 is inserted into a medullary canal of the femur 93, which is suitably widened for receiving the shaft 5. The shaft 5 can be held in the medullary canal 93 by an interference fit in the case of cementless implantation or can be secured with cement (not shown). The implantation and fastening of a femoral component of a knee joint prosthesis as such are basically known and therefore do not need to be explained in more detail.

Figure 3:
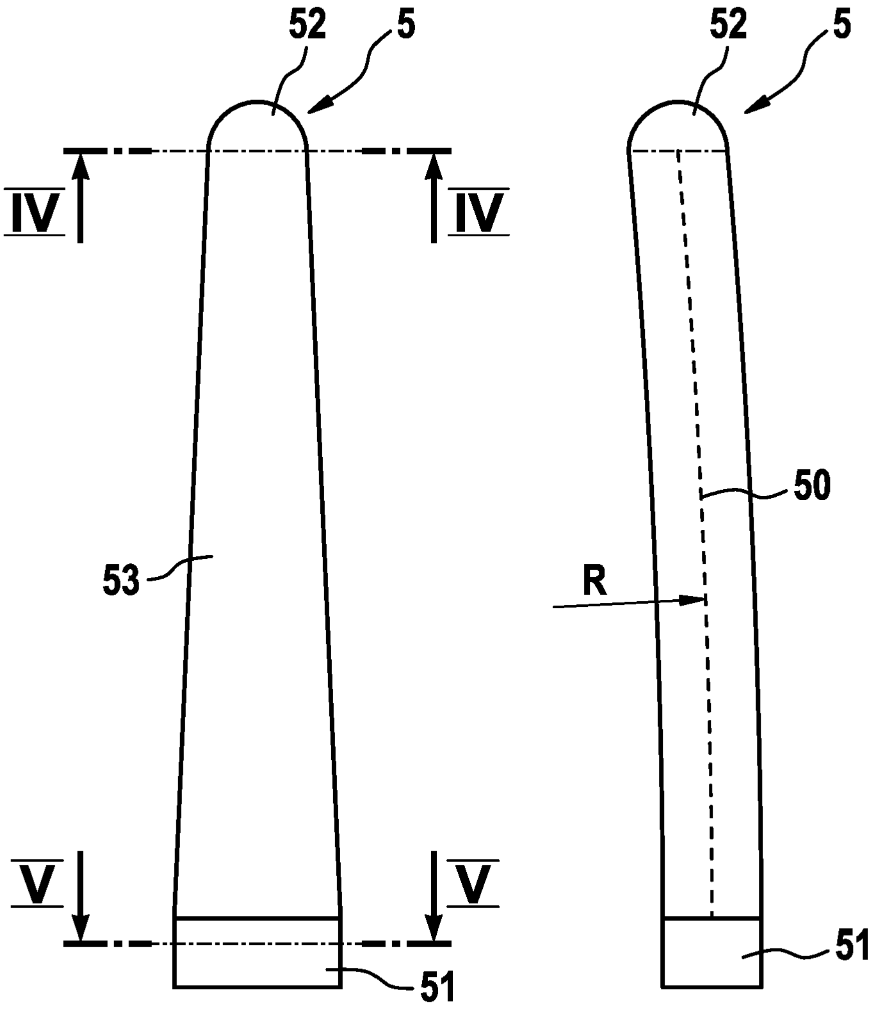

The shaft 5 is of a modular configuration in different sizes. Examples of different sizes of the shaft 5, 5' and 5" are shown in FIGS. 10*a, b, c*. The shaft 5 according to the invention is shaped in a particular way. FIG. 3*a* shows the shaft 5 in a frontal view, from which will be seen a straight conical shape with a thicker distal end 51 and a thinner proximal end 52.

Figure 4:
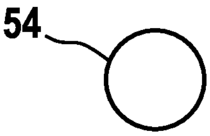
FIG. 4 shows a cross-sectional view of a proximal shaft end according to a line IV-IV in FIG. 3.
Figure 5:
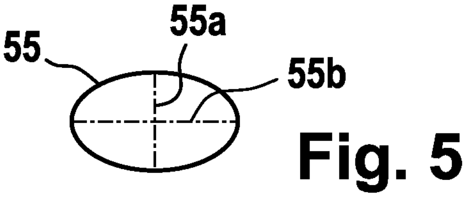
FIG. 5 shows a cross-sectional view of a distal shaft end according to a line V-V in FIG. 3.

The proximal end 52 is rounded in order to simplify the insertion of the shaft 5 into the medullary canal of the femur 93 and in order to reduce a traumatic effect. A view of the proximal end 52 is shown in FIG. 4. Accordingly, the cross-section 54 is circular at the proximal end 52. A view of the distal end 51 is shown as a cross-sectional view in FIG. 5. Accordingly, at the distal end 51, the cross-section 55 is oval, in particular elliptical. Here, the shorter axis 55*a* is in the AP direction, and the longer axis 55*b* is in the ML direction. A lateral surface 53 of the shaft 5 is therefore not conical, but forms a transition surface between an elliptical and a round cross-section.

In a side view from the lateral direction, the shaft 5 is likewise designed with conical tapering, but it is not straight in this plane and is instead provided with a weak curvature, as symbolized by the center line 50 shown in dashed lines in FIG. 4*b*. A radius of curvature R is thus relatively large, such that there is a weak curvature. In the illustrative embodiment shown, the radius of curvature R is 1500 mm.

Various alternatives to the design of the shaft 5 are shown in FIG. 6. They relate in particular to a design of the shaft 5 for cementless implantation (see FIG. 6*a*) and a design of the shaft 5* for cemented implantation (see FIG. 6*b*). The two shafts 5, 5* differ on the one hand in terms of the design of their lateral surface 53 and on the other hand in terms of their width.

Reference is now made to FIG. 7, which shows a rasp 13 (or a compressor). This is a tool for creating a cavity for receiving the shaft 5 in the femur 93. When the cavity is created, the medullary channel of the femur 93 is widened to the extent that it is dimensioned to receive the shaft 5. This applies to the dimensions in terms of width and depth and also in terms of the curvature (i.e. the rasp 13 is curved in the same way as the shaft 5). This is done with great precision in order to achieve a precise fit of the shaft 5. In the case of the shaft 5 provided for cementless implantation, this means that the cavity is widened only to the extent that an interference fit for the shaft is obtained. Specifically, this means that the tool used to widen the cavity, such as the rasp 13 shown in FIG. 7, has a somewhat smaller width than the associated shaft 5, namely reduced by an interference fit dimension 57 (symbolized in FIG. 7 by the dashed line on each side of the rasp 13). An example of such an interference fit dimension is 0.2 mm on each side. When the shaft 5 is inserted into the undersized cavity during implantation, this results in an interference fit which ensures secure anchoring even without cement. To increase the fastening security, it is expediently provided that the lateral surface 53 has a corrugation. The corrugation is provided with a multiplicity of grooves 59, specifically 24 grooves in the illustrative embodiment shown, as is indicated in FIG. 8*a*. This results in a firm fit, both in terms of an initial fastening and also in terms of a long-term stability of the fastening.

The shaft 5* provided for implantation with cement differs in the design of the lateral surface and in its width. The lateral surface is not provided with a corrugation, but with a small number of furrows 59*. As is shown in FIG. 8*b*, three furrows are preferably provided, specifically distributed equidistantly on the circumference of the lateral surface 53 with an angular spacing of 120°. As regards the width, the shaft 5* provided for implantation with cement is reduced by an undersize 58 at least in the region of the lateral surface 53. The undersize 58 here stands for the thickness of a cement jacket with which the shaft 5* is to be anchored in the medullary canal of the femur 93. As an example, FIG. 6*b* shows a thickness of the cement jacket of 1 mm, corresponding to a distance between the dashed and the dot-and-dash line. Furthermore, fastening by means of an interference fit is not provided for the shaft 5*, such that it is further reduced in terms of its width by the interference fit dimension 57. This reduction affords the advantage that one and the same rasp 13 can be used to create the required cavity, regardless of whether a shaft for cemented implantation 5* or a shaft for cementless implantation 5 is finally used. Thus, a uniform rasp can be used for each shaft size of the set, regardless of the type of fastening.

The shaft 5 is arranged on the joint element 4 by means of the adapter 6. The adapter 6 is designed as a double cone with a proximal cone 61 and a distal cone 62, which are connected in one piece via an incised region 60. The cone 61 is to be used for a cone connection in a corresponding seat 56 at the distal end of the shaft, and accordingly the distal cone 62 is to be inserted into a corresponding seat of a cone connection on the coupling piece 43 of the joint element. The adapter permits a largely free angle adjustability between shaft 5 and joint element 4, and, by plugging the cone connections together by means of adapter 6, this angular position is locked. Furthermore, a locking screw 65 is optionally provided, which secures the adapter 6 at the shaft side. Correspondingly, a securing means (not shown) can be provided at the joint side. A view of the angular variability between shaft 5 and joint element 4 by means of adapter 6 is shown in FIG. 11*a*. As is symbolized by the double arrow, the angular position of the shaft 5 can be changed freely. The transition between the shaft 5 in front of the adapter 6 can be seen in a detailed view in FIG. 11*b*, where an angle marking 85 is placed on the shaft 5 for visualizing an angular position.

The shafts 5 are available in different sizes with different lengths. Thus, there are shafts of normal length, as shown in FIG. 10*b*, short shafts 5', as shown in FIG. 10*a*, and long shafts 5", as shown in FIG. 10*c*. For example, the short shafts can be 30 mm shorter and the long shafts 30 mm longer than the shaft 5 of normal length. The adapters 6 are expediently also available in different lengths, the length of the adapters varying by a smaller amount than the length of the shafts 5. For example, a short adapter 6' can be 5 or 10 mm shorter than a normal-length adapter 6, or a long adapter 6" can be 5 or 10 mm longer than a normal adapter 6. Thus, by using a suitable adapter, fine adjustment of the length can be achieved, in addition to the already described function of the angle adjustability and locking.

Figure 12:
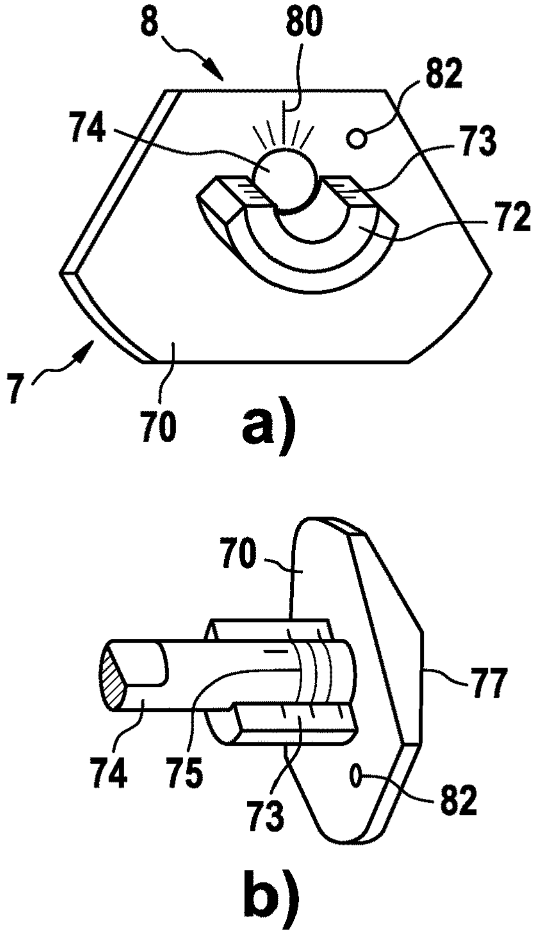

FIG. 12 shows a combined depth-measuring device 7 and angle-measuring device 8. It comprises an approximately trapezoidal base plate 70 with a central opening 74. A shaft of an implantation instrument, in particular a shaft 14 of the rasp 13, or of a drill can be inserted through this opening 74. This shaft is provided with markings 75 at a defined location. The depth-measuring device 7 has a half-shell-like attachment 72, which borders the opening 74 on one half. A depth marking 73 is arranged on an upper side of the attachment 72. An angled contact surface is formed on a rear side 77 of the base plate 70. During the implantation, this contact surface is placed on the shaft 14 of the rasp 13 inserted in the cavity created in the femur 93 and is brought to bear against an end face at the distal end of the femur 93. The base plate 70 thus adopts a defined position relative to the femur 93. The depth of the rasp 13 in the cavity in the femur 93 can then be read off by means of the marking 75 on the shaft 14 of the rasp 13, based on the depth marking 73 on the depth-measuring device 7.

The angle-measuring device is constructed accordingly.

It uses the same base plate 70. An angle scale 80 is also provided. It is also arranged bordering the opening 74, specifically at the top end thereof. Furthermore, an indicator 82 is provided, which can be designed as a punched opening. This characterizes the direction of a rotation, namely either toward the indicator 42 or away from it (as a replacement for perspective-dependent and therefore confusing left/right rotation indications). The angle scale 82 works together with a marking reference 81 on the shaft 14 (see FIG. 13). Here, advantage is taken of the fact that the rasp 13 is curved in the same way as the shaft 5. Thus, the shaft 5 will align in the cavity created by the rasp 13 in the same way as the rasp 13 itself. Thus, the rasp 13 can be used as a kind of trial implant. However, it is equally possible for an independent trial implant to be provided. By means of the angle scale 80, the angular position of the rasp 13 in the cavity in the femur 93 can now be determined on the basis of the marking 81 on the shaft and the indicator 82. With the information thus obtained concerning depth and angle position, the shaft 5 can be mounted in the correct angular position on the joint element 4 and the prosthesis can be inserted into the cavity created with the correct depth in the femur 93.

Figure 14:
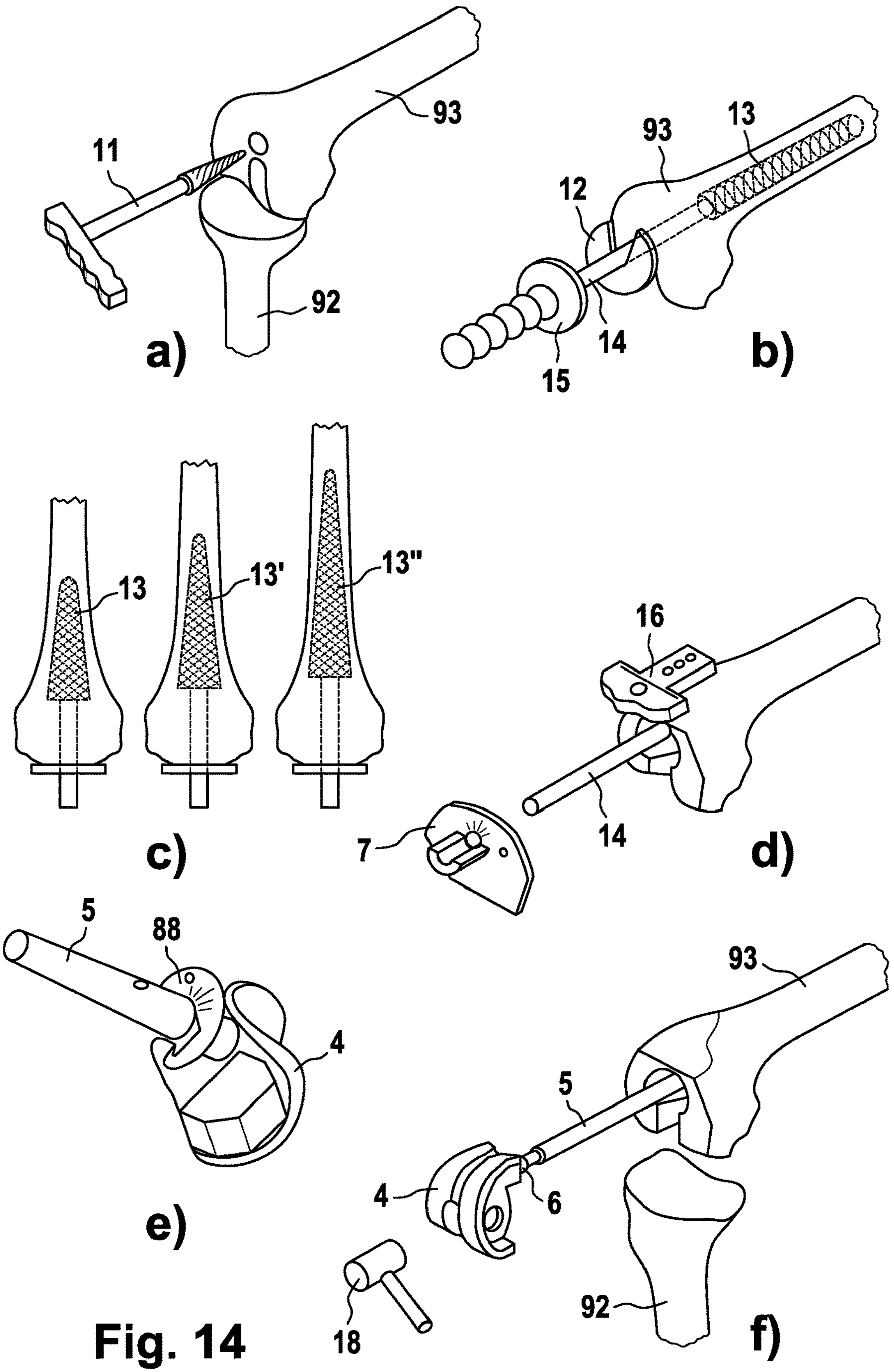

The individual steps in the implantation are shown in FIG. 14. In a first step 14*a*, an access route to the medullary canal in the femur 93 is opened by means of an awl or a drill 11 and initially drilled out. By means of the rasp 13, the medullary canal is widened, and the cavity for receiving the shaft 5 is thus created. To set a defined depth, a stop plate 12 is expediently provided, which is placed onto the shaft 14 of the rasp 13 (see FIG. 14*b*). In conjunction with a corresponding thickening 15 on the shaft 14 of the rasp 13, it can thus be ensured that the cavity is not widened beyond a certain depth. The medullary canal is then gradually widened in the manner known per se, until cortical contact is reached in the medullary canal. Rasps 13 of different lengths are advantageously made available; thus, if the fit with the smallest rasp is not sufficiently firm, a rasp of the same size (width) but of greater length can be selected in order thereby to establish safe cortical contact in the medullary canal. Such rasps of the same width (size) but of different lengths are shown as rasp 13' and rasp 13" in FIG. 14*c*.

Gauges can then be applied in a manner known per se, one of which is shown by way of example as gauge 16 in FIG. 14*d*. The necessary cuts are then made at the distal end of the femur in a manner likewise known per se. In order finally to determine the required adapter length, the depth-measuring device 7 is used. It is placed onto the shaft 14, and the depth is measured in the manner described above. Depending on the depth, an adapter 6 of suitable length can thus be selected. This permits fine adjustment of the depth. Furthermore, an angular position of the cavity and thus of the shaft 5 to be fastened in the femur 93 can be determined in the manner described. By means of an alignment gauge 88, which is temporarily arranged at the transition between the shaft and the joint element of the femoral component 3 (a separate trial prosthesis is preferably used here), a rotation angle between the shaft 5 and the joint element 4 is set (see FIG. 14*e*). Finally, this angle is also used to place the shaft 5 properly onto the adapter 6 and secure it using the cone connection. The femoral component 3 with joint element 4 and shaft 5 is thus correctly set in terms of length and (rotation) angle. By means of a (symbolically indicated) insertion tool 18, it can then be implanted at the prepared site at the distal end of the femur 93 (see FIG. 14*f*).

The invention claimed is:

1. A knee joint endoprosthesis set comprising:

modular knee joint endoprostheses in different sizes, each knee joint endoprosthesis comprising a tibial component for anchoring at a proximal end of the tibia, a femoral component for anchoring at a distal end of the femur, the femoral component comprising:

a joint element for articulated cooperation with the tibial component and a shaft configured for anchoring in a medullary canal of the femur, the set comprising shafts in different sizes, each shaft having a shape that tapers from a distal end, facing toward the joint element, to a proximal free end of the shaft, and is designed with an oval cross-section at the distal end and with a round cross-section in both a horizontal transverse plane and a coronal plane, forming a hemispherical shape at the proximal free end of the shaft, wherein an ovality defined by the oval cross-section increases as the size of the shafts increases, wherein the different sizes are graded according to the ovality, wherein the shafts each have a lateral surface, wherein the lateral surface extends from the distal end to the proximal free end, and wherein the lateral surface is a transition surface between the oval cross-section at the distal end and the round cross-section at the proximal free end, and wherein the ovality is elliptical.

2. The knee joint endoprosthesis set as claimed in claim 1, wherein the oval cross-section has an ovality of the kind whose major axis lies in a medial to lateral (ML) direction and whose minor axis lies in an anterior to posterior (AP) direction, wherein a ratio of the long axis to the short axis lies in the range of between 1.1 and 1.4.

3. The knee joint endoprosthesis set as claimed in claim 1, wherein a degree of ovality increases as the size of the shaft increases.

4. The knee joint endoprosthesis set as claimed in claim 1, wherein the lateral surface corresponds to a conical transition body between an oval cross-section at one end and a circular cross-section at the other end.

5. The knee joint endoprosthesis set as claimed in claim 1, wherein the shafts are curved, with a curvature that has a radius of curvature of in the range of between 1200 mm and 1800 mm.

6. The knee joint endoprosthesis set as claimed in claim 1, wherein the shafts are curved, wherein the curvature of the shafts in an anterior to posterior (AP) direction and a medial to lateral (ML) direction is different, wherein the shafts are more strongly curved in the AP direction, and not curved in the ML direction.

7. The knee joint endoprosthesis set as claimed in claim 1, wherein the shafts are designed as short shafts with a length of less than 7 times an equivalent diameter at the distal shaft end.

8. The knee joint endoprosthesis set as claimed in claim 1, wherein the free end of the shafts has a rounded dome shape, wherein the free end is rounded all the way around.

9. The knee joint endoprosthesis set as claimed in claim 1, wherein adapters are provided which are configured to connect the joint element to one of the shafts with a screw, wherein adapters are provided in different lengths, and wherein the adapters are configured to contact both the joint element and the shaft in a connected configuration, and wherein the adapters are one piece.

10. The knee joint endoprosthesis set as claimed in claim 9, wherein the adapters can be locked at an adjustable angle, and wherein the adapters are provided with a double cone.

11. The knee joint endoprosthesis set as claimed in claim 1, wherein shafts for fastening by means of cement and shafts for cementless fastening are provided, wherein the shafts for fastening by means of cement each have a predetermined undersize relative to the corresponding shafts for cementless fastening.

12. The knee joint endoprosthesis set as claimed in claim 11, wherein the shafts for fastening by means of cement have a smooth lateral surface or are provided with a maximum of five furrows, and/or the shafts for cementless fastening have a corrugated lateral surface.

13. The knee joint endoprosthesis set as claimed in claim 1, wherein the sizes of the shafts are graded regularly according to a medial to lateral (ML) dimension, on the basis of a module dimension.

14. The knee joint endoprosthesis set as claimed in claim 13, wherein there are between 8 and 14 different module dimension sizes.

15. An instrument kit for implanting a femoral component of a knee joint endoprosthesis from the knee joint endoprosthesis set as claimed in claim 1, wherein the femoral component has a shaft and a joint element, wherein the instrument kit comprises:

a tool for forming a cavity, dimensioned to receive the shaft, at the distal end of the medullary canal of a femur, a gauge for producing a seat for the joint element at the distal end of the femur, a depth-measuring device for determining a positioning of the shaft in the cavity created to receive the shaft, and an insertion instrument for implanting the femoral component at the distal end of the femur, wherein the depth-measuring device is designed to display a required length of the shaft and/or of an adapter for fastening the shaft to the joint element.

16. The instrument kit as claimed in claim 15, wherein an angle-measuring device is further provided, which is designed to determine a rotation angle of the shaft within the medullary canal, wherein a separate indicator for a rotation direction of the shaft within the medullary canal is provided.

17. The instrument kit as claimed in claim 16, wherein the depth-measuring device and the angle-measuring device are designed as a combined element.

18. A method for implanting a femoral component of a knee joint endoprosthesis from the knee joint endoprosthesis set as claimed in one claim 1, wherein the femoral component has a shaft and a joint element, the method comprising:

preparing a knee joint for the implantation of a knee joint endoprosthesis, forming a cavity at the distal end of the femur for receiving the shaft, producing a seat for the joint element at the distal end of the femur by means of a gauge, determining a positioning of the shaft in the cavity, and inserting the femoral component with its shaft and the joint element, wherein a suitable size of the shaft is selected from the knee joint endoprosthesis set.

19. The method as claimed in claim 18, the method further comprising:

selecting a suitable size of the shaft on the basis of a ML dimension, and/or determining a length of an adapter for fastening the shaft to the joint element by measuring a depth of the cavity, and selecting the corresponding adapter, and/or measuring an angular position for determining an angle of rotation of the shaft within the medullary canal, wherein a rotation direction of the shaft within the medullary canal is determined by means of a separate indicator, and/or measuring an angular position for determining an angle of rotation of the shaft within the medullary canal, wherein a rotation direction of the shaft within the medullary canal is determined by means of a separate indicator, preferably by setting a relative angle of rotation between shaft and joint element by means of the adapter.

20. The knee joint endoprosthesis set as claimed in claim 1, wherein the oval cross-section has an ovality of the kind whose major axis lies in a medial to lateral (ML) direction and extends from a first end of the major axis to a second end of the major axis and whose minor axis lies in an anterior to posterior (AP) direction and extends from a first end of the minor axis to a second end of the minor axis, and wherein a material of the shafts extends from the first end of the major axis to the second end of the major axis and extends from the first end of the minor axis to the second end of the minor axis.

21. The knee joint endoprosthesis set as claimed in claim 1, wherein the shaft comprises the oval cross-section at the distal end and with a round cross-section in a median plane at the proximal free end of the shaft.

* * * * *